(12) United States Patent
Ismail et al.

(10) Patent No.: US 8,501,250 B2
(45) Date of Patent: Aug. 6, 2013

(54) EXTRACTIONS OF FIXED OIL AND THYMOQUINONE RICH FRACTIONS (TQRF)

(75) Inventors: Maznah Ismail, Selangor Darul Ehsan (MY); Ghanya Al-Naqeeb, Selangor Darul Ehsan (MY); Kim Wei Chan, Selangor Darul Ehsan (MY); Raja Nurzatul Efa Adnan, Selangor Darul Ehsan (MY)

(73) Assignee: Universiti Putra Malaysia, Selangor Darul Ehsan (MY)

( * ) Notice: Subject to any disclaimer, the term of this patent is extended or adjusted under 35 U.S.C. 154(b) by 0 days.

(21) Appl. No.: 12/739,748

(22) PCT Filed: Aug. 7, 2009

(86) PCT No.: PCT/MY2009/000115
§ 371 (c)(1),
(2), (4) Date: Apr. 26, 2010

(87) PCT Pub. No.: WO2010/064891
PCT Pub. Date: Jun. 10, 2010

(65) Prior Publication Data
US 2012/0046366 A1    Feb. 23, 2012

(30) Foreign Application Priority Data
Dec. 4, 2008  (MY) ............................... PI 20084925

(51) Int. Cl.
*A61K 36/00*    (2006.01)
(52) U.S. Cl.
USPC .......................................... 424/776; 424/725

(58) Field of Classification Search
None
See application file for complete search history.

(56) References Cited

U.S. PATENT DOCUMENTS

2007/0243310 A1* 10/2007 Leonard et al. ............... 426/651
2008/0299234 A1* 12/2008 Schrezenmeir ............... 424/745
2010/0028468 A1*  2/2010 Pacioretty et al. ............ 424/732

FOREIGN PATENT DOCUMENTS

| IN | 200401890 | * | 9/2006 |
| JP | 2005-87998 A | | 4/2005 |
| KR | 10-0522206 B1 | | 10/2005 |
| KR | 10-2006-0093145 A | | 8/2006 |

OTHER PUBLICATIONS

Ei-Ghorab, A. J. Essential Oil-Bearing Plants. 2003. vol. 6, No. 2, pp. 67-77.*
Wawrzyniak et al. Inzynieria i Aparatura Chemiczna. 2004. vol. 43 (3, Spec. Issue), pp. 161-162.*
Alhaj et al. Am. J. Pharmacol. Toxicol. 2008. vol. 3, No. 4, pp. 225-228.*
International Search Report dated Feb. 2, 2010 (Three (3) pages).

* cited by examiner

*Primary Examiner* — Chris R Tate
(74) *Attorney, Agent, or Firm* — Crowell & Moring LLP

(57) ABSTRACT

The present invention reported that SFE is suitable for *Nigella sativa* seeds oil extraction and fractionation. TQRF that were produced through SFE extractions (600 bars/40° C.) and fractionations (100-200 bars/40-60° C.) possessed high level of TQ and antioxidant activity. SFE fractionation efficiently concentrates the TQ content and antioxidant activity of *Nigella sativa* seeds oil in short time and low cost manners without using any hazardous organic solvents.

17 Claims, 4 Drawing Sheets

EXTRACTIONS OF FIXED OIL AND THYMOQUINONE RICH FRACTIONS (TQRF)

This application is a national stage of PCT/MY2009/000115, filed Aug. 7, 2009, which claims priority under 35 U.S.C. §119 to PI 20084925, filed Dec. 4, 2008, the entire disclosure of which is herein expressly incorporated by reference.

FIELD OF INVENTION

The present invention is generally referred to extractions of fixed oil and thymoquinone rich fractions (TQRF).

BACKGROUND OF INVENTION

Nigella sativa L. belongs to the family of Ranuculaceae, which is known as food flavouring agents, food preservatives as well as health-promoting ingredients since few thousands years ago. Generally, Nigella sativa seeds contain more than 30% of fixed oil and 0.40% to 0.45% of volatile oil. Nigella sativa oil is considered as one of the excellent functional edible oil due to its advantage role in human nutrition as well as diseases prevention and treatment.

Thymoquionone (TQ) is the major bioactive component (18.4% to 24%) in Nigella sativa volatile oil. Many pharmacological researches reported that Nigella sativa oil and its bioactive compound, TQ possesses multiple health-beneficial activities, which include anti-tumor, anti-inflammatory, anti-bacterial, anti-diabetic, anti-hypertensive, hyperglycemic, anti-oxidatative and immuno-modulation activities.

Due to its multiple health benefits, extraction of TQ from Nigella sativa seeds is of prime importance and thus has received continuous attention from researchers and nutraceutical industry worldwide recently. However, the present methods (solvent extractions and hydro distillation) that are used in the oil extraction of Nigella sativa seeds are not only time-consuming, costly and environmental hazardous, it also imposes a threat to consumers' health if the organic solvents are not completely removed from the extractives. In this scenario, supercritical carbon dioxide fluid extraction (SFE) seems to be a better alternative for Nigella sativa seeds extraction. Advantageously, SFE offers the usage of non-toxic, non-explosive, environmental friendly, cost effective, time saving and selectivity-adjustable solvent (supercritical carbon dioxide fluid) in the extraction process. Further more, it also enables the oil extraction to be carried out under low temperature and oxygen-free condition. This feature is very crucial in the extraction of bioactive compounds that are highly susceptible to oxidative degradation, for instance TQ. On the other hand, simultaneous fractionation by using SFE enables the concentration of targeted bioactive compound such as TQ to be conducted in a solvent-free as well as time and cost saving manner.

The objective of this invention is to develop an extraction procedure to obtain Nigella sativa seeds oil and fractions that are high in bioactive compounds (such as TQ) and anti-oxidative activity through SFE extraction and fractionation.

SUMMARY OF INVENTION

Accordingly, there is provided a supercritical fluid extraction process for extracting a fixed oil from Nigella sativa seeds, the process includes the step of extracting Nigella sativa seeds crude oil at a pressure of between 300 to 600 bars and at temperature of between 31 to 80° C.

Also provided is supercritical fluid extraction process having a carbon dioxide feed of between 25 to 30 g/min for extracting Thymoquinone Rich Fractions (TQRF) from Nigella sativa seeds, the process includes the steps of (a) extracting Nigella sativa seeds crude oil at a pressure of between 300 to 600 bars and at temperature of between 31 to 80° C. and (b) fractionating Nigella sativa seeds crude oil obtained in step (a) at a pressure of 100 to 300 bars and at temperatures of 31 to 80° C.

Further there is also provided a supercritical fluid extraction process having a carbon dioxide feed of between 25 to 30 g/min for simultaneously extracting a fixed oil and Thymoquinone Rich Fractions (TQRF) from Nigella sativa seeds, the process includes the steps of (a) extracting Nigella sativa seeds crude oil at a pressure of between 300 to 600 bars and at temperature of between 31 to 80° C. and (b) fractionating Nigella sativa seeds crude oil obtained in step (a) at a pressure of 100 to 300 bars and at temperatures of 31 to 80° C.

The present invention consists of several novel features and a combination of parts hereinafter fully described and illustrated in the accompanying description and drawings, it being understood that various changes in the details may be made without departing from the scope of the invention or sacrificing any of the advantages of the present invention.

BRIEF DESCRIPTION OF THE DRAWINGS

The drawings constitute part of this specification and include an exemplary or preferred embodiment of the invention, which may be embodied in various forms. It should be understood, however, the disclosed preferred embodiments are merely exemplary of the invention. Therefore, the drawings attached herein are not to be interpreted as limiting, but merely as the basis for the claims and for teaching one skilled in the art of the invention.

DETAILED DESCRIPTION OF THE PREFERRED EMBODIMENTS

Figure 1:
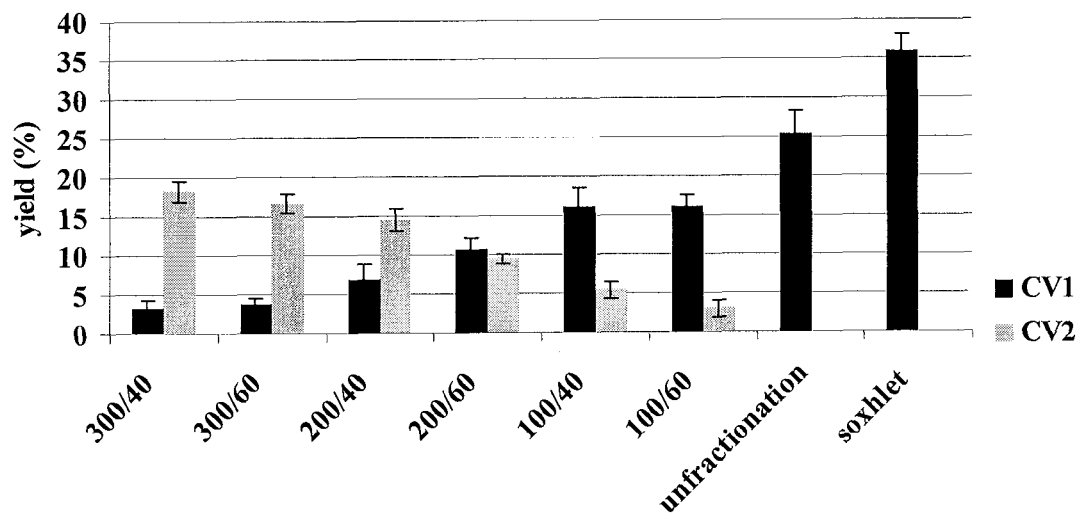
FIG. 1 shows the yield of different Nigella sativa seeds oil fractions (n=2)

The present invention is generally referred to extractions of fixed oil and thymoquinone rich fractions (TQRF). Hereinafter, this specification will describe the present invention according to the preferred embodiments of the present invention. However, it is to be understood that limiting the description to the preferred embodiments of the invention is merely to facilitate discussion of the present invention and it is envisioned that those skilled in the art may devise various modifications and equivalents without departing from the scope of the appended claims.

The present invention provides a SFE extraction procedure that allows the total oil extraction of Nigella sativa seeds and TQ concentration of Nigella sativa oil fraction to be carried out simultaneously. Through the present invention, high anti-oxidative TQRF from Nigella sativa seeds could be obtained in a shorter time and lower cost manner without using any further purification processes that involved usage of hazardous organic solvents as well as expensive equipments. Besides producing TQRF, the present invention also simultaneously produces large amount of Nigella sativa seeds fixed oil (NSO) that might possess other economical values. NSO could be the major ingredient in lower range of *Nigella sativa* nutraceutical and cosmoceutical products such as functional cooking oil, facial cream and so on. Thus, the present invention also contributes to the wastage reduction and functionality diversification of *Nigella sativa* seeds oil.

Generally, the present invention provides extractions of fixed oil and TQRF from *Nigella sativa* seeds including the steps of extracting *Nigella sativa* seeds crude oil at a pressure of between 300 to 600 bars and at temperature of between 31 to 80° C. and fractionating *Nigella sativa* seeds crude oil obtained in step (a) at a pressure of 100 to 300 bars and at temperatures of 31 to 80° C.

The extractions can be independent i.e. the fixed oil and TQRF can be extracted separately or simultaneous extractions.

In the preferred embodiments of the present invention, the supercritical fluid is supercritical carbon dioxide and the extractions are based on sample size of 100 g of cleaned, dried and ground *Nigella sativa* seeds.

Reference will be made to following examples and these examples are intended to be illustrative and not limiting.

Selection of SFE Parameters for Fractionation a. Sample Preparation

*Nigella sativa* seeds were cleaned and dried in oven at 40° C. until constant weight attained. Then, 100 g of the seeds were ground into powder by using electrical grinder (Waring Blender) for 1 min. This procedure should be performed just before the SFE extraction was initiated.

b. SFE Extraction

*Nigella sativa* seeds were extracted by using Supercritical Carbon Dioxide Extractor (Thar 1000 F) at 4 different extraction parameters (pressure (bars)/temperature (° C.) as follows: 400 bars/40; 600/40; 600/60; 600/80). Briefly, one hundred grams of ground *Nigella sativa* seed was placed into a 1 liter extraction vessel. After the extraction vessel was tightly sealed, the desired extraction temperature was set. Pressure within the extraction vessel was built up with a constant carbon dioxide flow rate (30 g/min) and regulated by automated back pressure regulator. The SFE extraction was initiated after the desirable temperature and pressure were achieved. The entire extraction process lasted for 3 hours and oil samples were collected from collection vessel after each interval of one hour. The total oil yield from the extraction was calculated through the accumulation of interval yields.

c. Determination of TQ Content in *Nigella sativa* SFE Oils

TQ content in *Nigella sativa* oils was determined by using analytical HPLC (Agilent 1100), completed with $C_{18}$ reversed-phase column (Zorbax SB-C18). Mobile phase was consisted of water, methanol (Fisher Scientific) and iso-propanol (Fisher Scientific) at the ratio of 50:45:5 (v/v), respectively. Flow rate of the mobile phase was set at 1.5 ml min$^{-1}$. *Nigella sativa* oils were initially dissolved in isopropanol and filtered through 0.45 μm Millipore filter prior to the injection (20 μl) into HPLC system. Thymoquinone contents of *Nigella sativa* SFE oils were determined through Thymoquinone standard (Sigma) curve and expressed in mg TQ/g oil.

d. Results

TABLE 1

Oil yield of *Nigella sativa* seeds oils extracted by SFE (n = 3)

| SFE Parameters | Oil Yield At Each Hour of SFE Extraction (%, w/w); | | | Accumulated yield (%, w/w) |
|---|---|---|---|---|
| | 1$^{st}$ hour | 2$^{nd}$ hour | 3$^{rd}$ hour | |
| 400 bars/ 40° C. | — | — | — | 19.32 $^a$ ± 0.81 |
| 600 bars/ 40° C. | 18.81 ± 0.22 | 5.08 ± 0.48 | 4.02 ± 0.70 | 27.92 $^b$ ± 1.27 |
| 600 bars/ 60° C. | 19.24 ± 0.65 | 5.78 ± 0.47 | 4.55 ± 0.37 | 29.47 $^b$ ± 1.26 |
| 600 bars/ 80° C. | 24.44 ± 0.38 | 7.34 ± 0.95 | 5.08 ± 0.09 | 36.87 $^c$ ± 0.81 |

$^{a\text{-}c}$ Different alphabets within same column indicated significant difference (P < 0.05).

TABLE 2

TQ content of *Nigella sativa* seeds oils extracted by SFE (n = 3)

| SFE Parameters | TQ content in the oil At Each Hour of SFE Extraction (g TQ/100 g oil) | | | Accumulated TQ content in the oil (mg TQ/g oil) | Accumulated TQ content in total oil yield (g TQ/100 g seeds) |
|---|---|---|---|---|---|
| (bars/° C.) | 1$^{st}$ hour | 2$^{nd}$ hour | 3$^{rd}$ hour | | |
| 600/40 | 2.77 ± 0.20 | 0.93 ± 0.18 | 0.49 ± 0.09 | 21.01 $^a$ | 0.587 |
| 600/60 | 2.49 ± 0.38 | 1.08 ± 0.53 | 0.79 ± 0.64 | 19.59 $^a$ | 0.577 |
| 600/80 | 2.10 ± 0.16 | 0.70 ± 0.10 | 0.52 ± 0.04 | 16.02 $^b$ | 0.590 |

$^{a\text{-}b}$ Different alphabets within same column indicated significant difference (P < 0.05).

Tables 1 and 2 show the yield and TQ content of *Nigella sativa* seeds oils extracted by SFE, respectively. Result indicates that a rise in extraction pressure from 400 bars to 600 bars under isothermal condition (40° C.) significantly increases the yield of *Nigella sativa* oil (P<0.05). Besides, results also indicate that a rise in SFE extraction temperature at constant pressure of 600 bars significantly increases the yield obtained but reduced the TQ content in the oil (P<0.05). SFE extraction at 600 bars coupled with temperature ranging from 40-80° C. efficiently extracted most of the oil and TQ (>50% from the total extractable matter) from *Nigella sativa* seeds in the first hour of extraction. However, a descending fall in oil yield and TQ content was observed in the subsequent two hours of extraction. Through this experiment, 600 bars/40° C. was chosen as the SFE parameters for further fractionation due to its high TQ content and low energy (heat) requirement.

Production of High Antioxidative TQRF from *Nigella sativa* Seeds through SFE Fractionation a. Sample Preparation

*Nigella sativa* seeds were cleaned and dried in oven at 40° C. until constant weight attained. Then, 100 g of the seeds were ground into powder by using electrical grinder (Waring Blender) for 1 min. This procedure should be performed just before the SFE extraction was initiated.

b. SFE Extraction and Fractionation

*Nigella sativa* seeds were extracted (600 bars/40° C.) and fractionated by using Supercritical Carbon Dioxide Extractor (Thar 1000 F) at 9 different fractionation parameters (pressure (bars)/temperature (° C.)) as followed: 300 bars/40° C., 300 bars/60° C., 200 bars/40° C., 200 bars/60° C., 100 bars/40° C., 100 bars/60° C. Briefly, one hundred grams of ground *Nigella sativa* seed was placed into a 1 liter extraction vessel. After the extraction vessel was tightly sealed, the extraction temperature was set at 40° C. Pressure within the extraction vessel was built up with a constant carbon dioxide flow rate (25 g/min) and regulated by automated back pressure regulator. The SFE fractionation was initiated after the extraction vessel reached 600 bars and 40° C. Fractionation of *Nigella sativa* oil was carried out in a first collection vessel 1 by regulating the inner pressure and temperature of the vessel according to 6 different designed fractionation parameters: (pressure (bars)/temperature (° C.): 300 bars/40° C., 300 bars/60° C., 200 bars/40° C., 200 bars/60° C., 100 bars/40° C., 100 bars/60° C.). At the same time, the condition of second collection vessel was set at atmospheric pressure (1 bar) and room temperature (25° C.) in order to collect the all the extractives from fractionation in the first vessel. The entire extraction and fractionation processes lasted for 2.5 hours. After the extraction was completed, the extraction vessel and the first collection vessel were depressurized and the fractions were collected from the first collection vessel and the second collection vessel, respectively. The yield of *Nigella sativa* fractions in first collection vessel and the second collection vessel were calculated finally. SFE unfractionated and petroleum ether extracted (Soxhlet, AOAC method) *Nigella sativa* oils were used as the subjects for comparison in this example.

c. Solvent Extraction by Using Soxhlet Method

Solvent extraction by using soxhlet method (AOAC method) was done and the solvent used is petroleum ether. First, 10 grams of ground *Nigella sativa* seeds were weighed and transferred into an extraction thimble. Then, the thimble was transferred into a soxhlet extractor (Witeg, Germany) and a weighed flask was attached. 200 ml of petroleum ether was added into the flask. The apparatus was connected to the condenser and water tap was turned on. The extraction was done for 8 hours on an electro thermal extraction unit. After 8 hours, the flask containing the petroleum ether was removed. The petroleum ether was evaporated under reduced pressure. The flask then was transferred into a vacuum oven for 1 hour to dry the extract. Finally, the flask was cooled down in a desiccator and the yield of the fractions was calculated.

d. Determination of TQ Content in *Nigella sativa* SFE Fractions

TQ contents in *Nigella sativa* fractions were determined by using analytical HPLC (Agilent 1100), which was completed with $C_{18}$ reversed-phase column (Zorbax SB-C18). Mobile phase was consisted of water, methanol (Fisher Scientific) and iso-propanol (Fisher Scientific) at the ratio of 50:45:5 (v/v), respectively. Flow rate of the mobile phase was set at 1.5 ml min$^{-1}$. *Nigella sativa* fractions were initially dissolved in isopropanol and filtered through 0.45 µm Millipore filter prior to the injection (20 µl) into HPLC system. Thymoquinone contents of *Nigella sativa* SFE fractions were determined through Thymoquinone standard (Sigma) curve and expressed in mg TQ/g fraction.

e. DPPH Radical Scavenging Activity of *Nigella sativa* SFE Fractions

DPPH radical scavenging activity of *Nigella sativa* SFE fractions was measured. α-tocopherol was used as the standard lipophilic antioxidant in this test. In brief, 0.1 ml of toluenic sample solution at different concentrations was added with 0.39 ml of fresh toluenic DPPH solution (0.1 mM). Then, the mixture was shaken vigorously and left in darkness for 60 minutes. Finally, the absorbance of the mixture was measured against pure toluene (blank) at 515 nm by using a UV-Visible spectrophotometer (Pharmaspec uv-1700, Shimadzu). DPPH scavenging activity of *Nigella sativa* SFE fractions were determined through α-tocopherol standard curve and expressed in mg α-tocopherol equivalent (Teq)/g sample.

f. Galvinoxyl Radical Scavenging Activity of *Nigella sativa* SFE Fractions

Galvinoxyl radical scavenging activity of *Nigella sativa* SFE fractions was measured. α-tocopherol was used as the standard lipophilic antioxidant in this test. In brief, 20 mg of oil sample (in 200 µl of toluene) was allowed to react with 200 µl of a toluenic solution of galvinoxyl (0.125 mM) for 60 minutes. Subsequently, the antiradical activity was of the samples was measured at room temperature by using ESR (JEOL, Japan) at the following conditions: center field=336.374±5 mT; sweep time=1 minute; microwave power=4 mW; modulation frequency=100 kHz; modulation width=0.08 mT; amplitude=60 and time constant=0.1 second. Galvinoxyl radical scavenging activity of *Nigella sativa* SFE fractions were determined through α-tocopherol standard curve and expressed in mg α-tocopherol equivalent (Teq)/g sample g. Results The results of this test are illustrated in the accompanying figures. FIG. 1 shows yield of different *Nigella sativa* seeds oil fractions. Result indicates that Soxhlet extraction yielded higher percentage of oil from *Nigella sativa* seeds as compared to all SFE extractions (P<0.05). Besides, result also indicates that a reduction in fractionation pressure would decrease (P<0.05) the fraction yield obtained in the second collection vessel. whereas variance in fractionation temperature did not alter the yield of the fractions in most of the cases (P>0.05).

Figure 2:
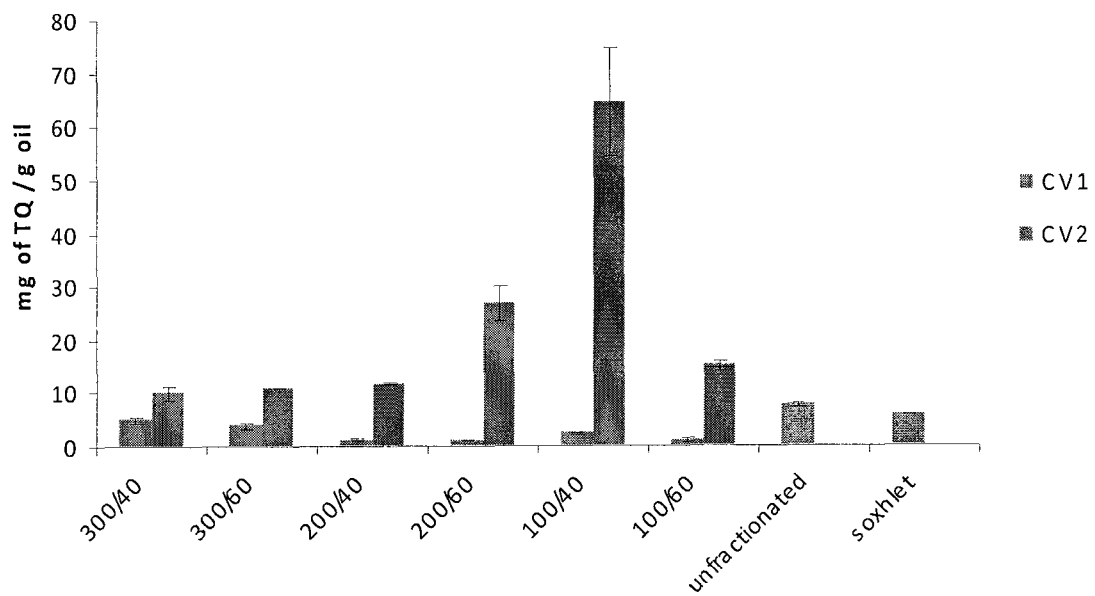
FIG. 2 shows the TQ concentration of different Nigella sativa seeds oil fractions (n=2)

FIG. 2 shows TQ concentration of different *Nigella sativa* seeds oil fractions. Result indicates that fractionation at 100 bars/40° C. efficiently increased the TQ content in *Nigella sativa* oil by approximately 10 folds as compared to unfractionated and Soxhlet samples (P<0.05). On the other hand, the content of TQ in 100 bars/40° C. fraction (~6.5% w/w of oil) was approximately 100 folds higher than TQ content in *Nigella sativa* oil (0.05% w/w of oil) that was reported in prior art.

Figure 3:
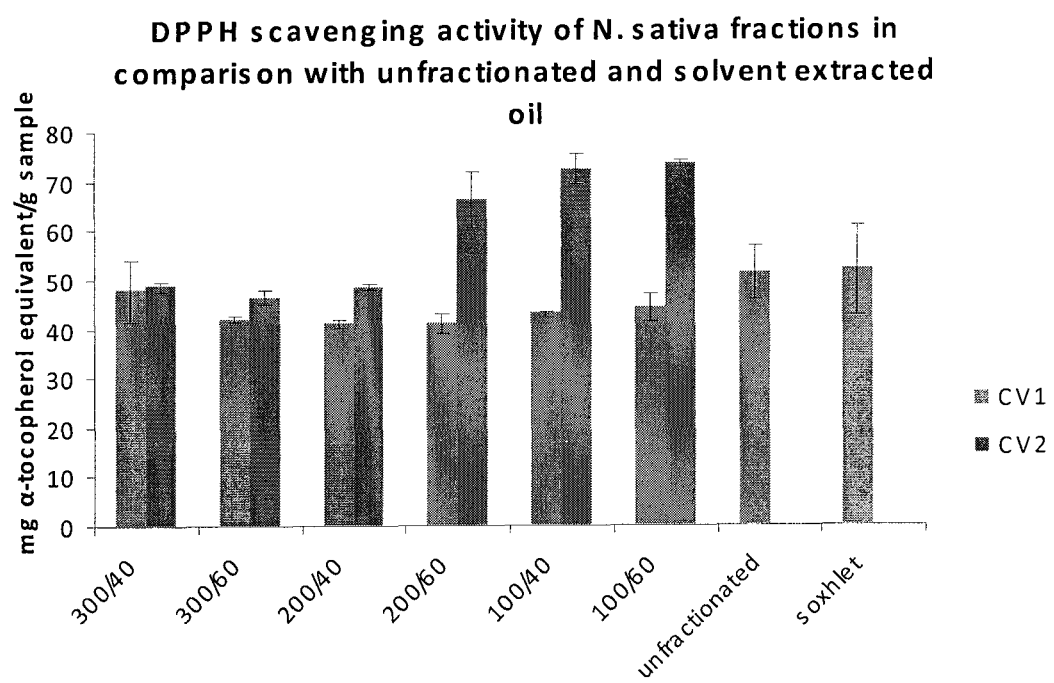
FIG. 3 shows the DPPH radical scavenging activity of different Nigella sativa seeds oil fractions (n=2)
Figure 4:
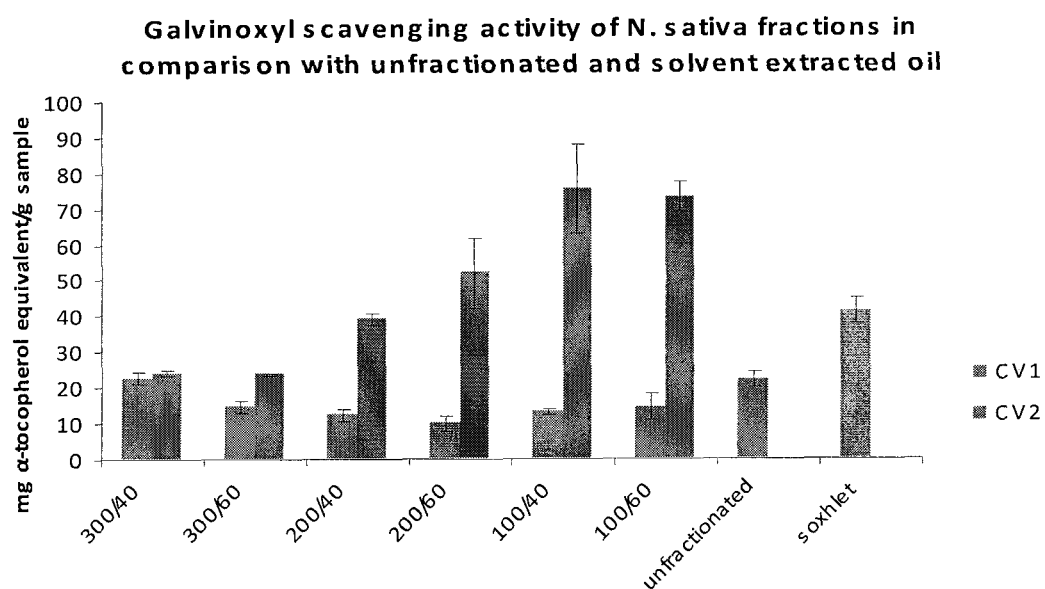
FIG. 4 shows the galvonoxyl scavenging activity of different Nigella sativa seeds oil fractions (n=2).

FIGS. 3 and 4 show DPPH and galvinoxyl radical scavenging activities of different *Nigella sativa* seeds oil fractions. Result indicates that fractionation at 100 bars/40° C. and 100 bars/60° C. greatly improved the antiradical activity of *Nigella sativa* oil towards DPPH and galvinoxyl radicals as compared to unfractionated and Soxhlet samples (P<0.05). In conclusion, fractionation at 100 bars/40° C. was found to be the best SFE fractionation parameters in producing high antioxidative TQRF due to its high content of TQ and great improvement in antioxidant activity.

As shown in the FIGS., the manipulation of various parameters such as pressure and temperature enables the optimization of the yield. For an example, a rise of extraction pressure from 400 bars to 600 bars in isothermal condition (40° C.) increases the oil yield from 19.32% to 27.919%. On the other hand, a rise of extraction temperature from 40 to 80° C. in isobaric condition (600 bars) increases the oil yield from 27.919% to 36.87%. A decrease of extraction temperature from 80 to 40° C. in isobaric condition (600 bars) increases the TQ content in the oil from 0.08% to 0.2% (w/w). Extraction pressure at 600 bars coupled with extraction temperature at 40° C. is the optimum SFE parameters selected for further fractionation in order to produce oil and TQRF from Nigella sativa seeds simultaneously.

The carbon dioxide feed is between 25 to 30 g/min and the extraction duration is between 2.5 to 3 hours after the extraction vessel reached the extraction pressure of 400 to 600 bars and the extraction temperature of 40 to 80° C.

It is noted that the SFE is suitable for *Nigella sativa* seeds oil extraction, wherein extraction pressure ranges from 400 to 600 bars coupled with extraction temperature ranging from 40 to 80° C. that result in oil yield ranging from 19.32% to 36.87% (w/w).

Extraction pressure at 600 bars coupled with extraction temperature at 80° C. results in highest oil yield (36.87%). At the same time, extraction pressure at 600 bars coupled with extraction temperature at 40° C. results in highest TQ content in the oil (0.2%).

At isobaric (600 bars) SFE extraction at extraction temperature ranging from 40 to 80° C. efficiently extracted most of the oil and TQ (>50% from the total extractable matter) from *Nigella sativa* seeds in the first hour of extraction.

The process provides oil yield ranging from 3.84 to 36.01% TQ content ranging from 5.7 to 64.5 mg of TQ/g oil. It is noted that a descending fall in oil yield and TQ content was observed in the second and third hour of extraction.

Soxhlet *Nigella sativa* seeds oil as shown in FIGS. 1 to 4 is obtained through Soxhlet extraction by using petroleum ether according to AOAC standard. It is noted that Soxhlet extraction yields higher than all SFE extractions and fractionations. Soxhlet extraction yields lower TQ content than all SFE extractions and fractionations. Fractionation of *Nigella sativa* seeds oil yields higher TQ content than Soxhlet (4.3 to 58.8 mg TQ/g oil higher) and unfractionated (2.4 to 56.9 mg TQ/g oil higher) *Nigella sativa* seed oil.

Unfractionated and Soxhlet *Nigella sativa* seeds oils are produced for comparison purpose. Fractionations of *Nigella sativa* seed oil at pressures of 100 to 300 bars and at temperatures of 40 to 60° C. by using supercritical fluid extraction reduce the total oil yield obtained ranging from 3.8% to 6.1% as compared to unfractionated oil.

An increase of fractionation temperature from 40 to 60° C. in isobaric condition (100, 200 and 300 bars, respectively) increases the oil yield in a first collection vessel but decrease the oil yield in a second collection vessel, correspondently. On the other hand, an increase of fractionation temperature from 100 to 300 bars in isothermal condition (40 and 60° C., respectively) decrease the oil yield in a first collection vessel but increase the oil yield in a second collection vessel, correspondently.

It is noted that each gram of *Nigella sativa* seeds oils or fractions provides antioxidant activity which is similar to 40.96 to 73.68 mg α-tocopherol through DPPH radical scavenging activity test. Similarly, each gram of *Nigella sativa* oils or fractions provides antioxidant activity, which is similar to 12.26 to 73.44 mg α-tocopherol through galvinoxyl radical scavenging activity test.

*Nigella sativa* seeds fractions produced at an extraction pressure of 600 bars and an extraction temperature of 40° C. followed by a fractionation pressure of 100 to 200 bars and an fractionation temperature of 40 to 60° C. exhibit better antioxidant activities than Soxhlet and unfractionated oils (2.4 to 56.9 mg TQ/g oil higher) through DPPH and galvinoxyl radical scavenging activity tests.

It is noted that the TQRF obtained from the extractions of *Nigella sativa* seeds oil possesses higher TQ content and antioxidant activity than SFE-unfractionated *Nigella Sativa* seeds oil and conventional solvent (petroleum ether) extracted oil. This is because other antioxidative compounds such as α-tocopherol, tocotrienol and phytosterols and so on might also contribute to the antioxidant activities of TQRF.

It must also be appreciated that the process as described above can be used for concentrating other volatile bioactive compounds.

The invention claimed is:

1. A supercritical fluid extraction process for extracting Thymoquinone Rich Fractions (TQRF) from *Nigella sativa* seeds, the process comprising the steps of:
   (a) extracting the crude oil of *Nigella sativa* seeds at a pressure of between 300 to 600 bars and at temperature of between 31 to 80° C.; and
   (b) fractionating the crude oil obtained in step (a) at a pressure of 100 to 300 bars and at temperatures of 31 to 80° C.;

wherein the process comprises a carbon dioxide feed of between 25 to 30 g/min.

2. The process as claimed in claim 1, wherein the process is conducted for a period of between 2 to 3 hours.

3. The process as claimed in claim 1, wherein the supercritical fluid is supercritical carbon dioxide.

4. The process as claimed in claim 1, wherein the process is conducted with a sample size of 100 g of cleaned, dried and ground *Nigella Sativa* seeds.

5. The process as claimed in claim 1, wherein the TQ content in the Thymoquinone Rich Fractions (TQRF) obtained by using a temperature of 80° C. and a pressure of 600 bars is 0.08%.

6. The process as claimed in claim 1, wherein the TQ content in the Thymoquinone Rich Fractions (TQRF) obtained by using a temperature of 40° C. and a pressure of 600 bars is 0.2%.

7. The process as claimed in claim 1, wherein the TQ content in the Thymoquinone Rich Fractions (TQRF) ranges from 5.7 to 64.5 mg of TQ per gram of oil.

8. The process as claimed in claim 1, wherein the TQRF exhibits antioxidant activity.

9. The process as claimed in claim 7, wherein the TQRF contains α-tocopherol, tocotrienol and phytosterols which enhance the antioxidant activity of the TQRF.

10. A supercritical fluid extraction process for simultaneously extracting a fixed oil and Thymoquinone Rich Fractions (TQRF) from *Nigella sativa* seeds, the process comprising the steps of:
    (a) extracting the crude oil of *Nigella sativa* seeds at a pressure of between 300 to 600 bars and at temperature of between 31 to 80° C.; and
    (b) fractionating the crude oil of *Nigella sativa* seeds obtained in step (a) at a pressure of 100 to 300 bars and at temperatures of 31 to 80° C.;

wherein the process comprises a carbon dioxide feed of between 25 to 30 g/min.

11. The process as claimed in claim 10, wherein the process is conducted for a period of between 2 to 3 hours.

12. The process as claimed in claim 10, wherein the supercritical fluid is supercritical carbon dioxide.

13. The process as claimed in claim 10, wherein the process is conducted with a sample size of 100 g of cleaned, dried and ground *Nigella Sativa* seeds.

14. The process as claimed in claim 10, wherein the TQ content in the Thymoquinone Rich Fractions (TQRF) obtained by using a fractionation temperature of 40 to 80° C. and a fractionation pressure of 100 to 300 bars ranges from 2 to 65 folds in TQRF than in fixed oil.

15. The process as claimed in claim 10, wherein each gram of said fixed oil or Thymoquinone Rich Fractions (TQRF) exhibit antioxidant activity that is equivalent to 12 to 75 mg of α-tocopherol.

16. The process as claimed in claim 10, wherein the antioxidant activity of TQRF is 7 folds higher than said fixed oil.

17. The process as claimed in claim 15, wherein the TQRF contains α-tocopherol, tocotrienol and phytosterols which enhance the antioxidant activity of the TQRF.

* * * * *